US 6,718,212 B2
Apr. 6, 2004

(54) IMPLANTABLE MEDICAL ELECTRICAL LEAD WITH LIGHT-ACTIVATED ADHESIVE FIXATION

(75) Inventors: Andrew J. Parry, 26 Cavendish Road, Henleaze, Bristol (GB), BS9 4EA; Terrell M. Williams, Brooklyn Park, MN (US)

(73) Assignees: Medtronic, Inc., Minneapolis, MN (US); Andrew J. Parry, Bristol (GB)

( * ) Notice: Subject to any disclaimer, the term of this patent is extended or adjusted under 35 U.S.C. 154(b) by 317 days.

(21) Appl. No.: 09/977,101

(22) Filed: Oct. 12, 2001

(65) Prior Publication Data

US 2003/0074041 A1 Apr. 17, 2003

(51) Int. Cl.$^7$ ................................................. A61N 1/05
(52) U.S. Cl. ........................ 607/130; 607/129; 600/391
(58) Field of Search ................. 607/129, 130, 607/119; 600/375, 386, 391

(56) References Cited

U.S. PATENT DOCUMENTS

| | | | |
|---|---|---|---|
| 3,737,579 A | 6/1973 | Bolduc | 128/418 |
| 4,010,758 A | 3/1977 | Rockland et al. | 128/418 |
| 4,282,886 A | 8/1981 | King | 128/785 |
| 4,313,448 A | 2/1982 | Stokes | 128/785 |
| 4,357,946 A | 11/1982 | Dutcher et al. | 128/785 |
| 4,727,880 A | 3/1988 | Roberts | 128/640 |
| 4,768,523 A | 9/1988 | Cahalan et al. | 128/785 |
| 5,423,806 A | 6/1995 | Dale et al. | 606/15 |
| 5,423,878 A | 6/1995 | Franz | 607/122 |
| 5,445,608 A | 8/1995 | Chen et al. | 604/20 |

(List continued on next page.)

OTHER PUBLICATIONS

Brochure, "Solutions That Cure," Loctite Corporation (2000).

Cazeau et al., "Four Chamber Pacing in Dilated Cardiomyopathy," *PACE*, p. 1974–79, Nov. 1994.

*Primary Examiner*—Kennedy Schaetzle
(74) *Attorney, Agent, or Firm*—Girma Wolde-Michael

(57) ABSTRACT

Medical electrical leads adapted to be implanted within the body, and particularly such leads having at least one distal electrode affixed at a site of a body organ, particularly the epicardium of the heart, employing a light-activated adhesive fixation, and methods and systems for accessing the site, applying the distal electrode to the site, and activating the light-activated adhesive. The lead is preferably implanted by performing a thoracoscopy of the thorax of the patient to visualize the site of the epicardium through a thoracoscope and to provide a pathway to the site of the epicardium. While viewing the site of the epicardium through the thoracoscope, the electrode head is inserted through the provided pathway to apply the plate against the site of the epicardium, and the light-activated adhesive is exposed to a predetermined bandwidth of light to adhere the plate to the epicardium. An elongated introduction tool is selectively operable to grasp and release the electrode head and to conduct light of the predetermined bandwidth to the electrode plate. The introduction tool preferably has an opaque sidewall enclosing a plurality of optical fibers distributed around the circumference of and within the sidewall of the introduction tool to extend lengthwise to the introduction tool distal end, whereby the plurality of optical fiber distal ends are capable of emitting light of the predetermined frequency in a substantially cylindrical emission pattern. The light-activated adhesive comprises one of a light-activated acrylic or cyanoacrylate adhesive that is activated by ultraviolet light that is activated by ultraviolet light. The lead body is formed with a strain relief proximal to the electrode head for absorbing strain placed on the lead body from being transmitted to the electrode head at the lead body distal end and absorbing the strain induced in the lead body by movement of the body organ, e.g., the contraction and expansion of the heart.

43 Claims, 5 Drawing Sheets

U.S. PATENT DOCUMENTS

| | | | |
|---|---|---|---|
| 5,464,447 A | 11/1995 | Fogarty et al. | 607/129 |
| 5,716,392 A | 2/1998 | Bourgeois et al. | 607/132 |
| 5,795,331 A | 8/1998 | Cragg et al. | 604/96 |
| 5,827,265 A | 10/1998 | Glinsky et al. | 606/8 |
| 5,871,532 A | 2/1999 | Schroeppel | 607/128 |
| 5,902,324 A | 5/1999 | Thompson et al. | 607/9 |
| 6,121,341 A | 9/2000 | Sawhney et al. | 522/84 |
| 6,219,579 B1 | 4/2001 | Bakels et al. | 607/17 |
| 6,398,797 B2 * | 6/2002 | Bombard et al. | 606/153 |

* cited by examiner

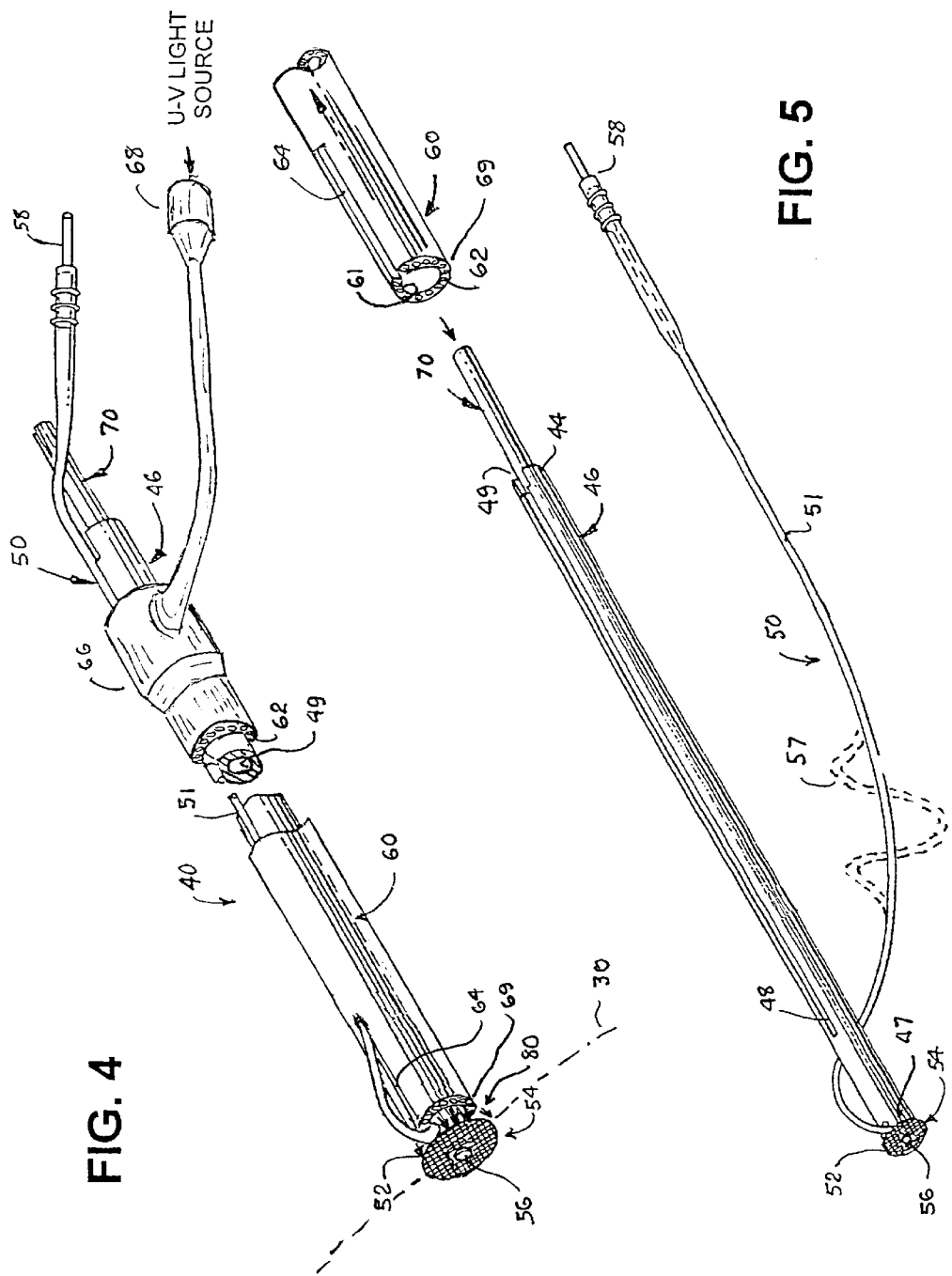

IMPLANTABLE MEDICAL ELECTRICAL LEAD WITH LIGHT-ACTIVATED ADHESIVE FIXATION

FIELD OF THE INVENTION

The present invention pertains to medical electrical leads adapted to be implanted within the body, and particularly to such leads having at least one distal electrode affixed at a site of a body organ, particularly the epicardium of the heart, employing a light-activated adhesive fixation and methods and systems for accessing the site, applying the distal electrode to the site and activating the light-activated adhesive.

BACKGROUND OF THE INVENTION

In the field of cardiac stimulation, cardiac pacing leads having bipolar and unipolar pace/sense electrodes have long been used in conjunction with implantable pulse generators (IPGs) to conduct pacing pulses or cardioversion/defibrillation shocks generated by the IPG to a site of the heart and cardiac signals from the site to the IPG. Cardioversion/defibrillation leads and pacing leads are typically provided with a passive fixation or an active fixation mechanism at the lead body distal end that is passively or actively engaged with cardiac tissue to anchor a distal tip electrode at a desired site in or on the heart. Passive fixation generally involves an atraumatic fixation lodging the distal electrode against the endocardium or within a coronary blood vessel. Positive or active fixation generally involves a more traumatic penetration of a fixation mechanism into the myocardium from an endocardial or epicardial surface, and the active fixation mechanism commonly comprises a distal electrode.

Endocardial pacing and cardioversion/defibrillation leads having either active fixation or passive fixation mechanisms are implanted by a transvenous route into a heart chamber to locate the distal electrode(s) at a selected site in the heart chamber where an active or passive fixation mechanism is deployed to maintain the electrode affixed at the site. Epicardial leads are implanted by exposure of the epicardium of the heart typically through a limited subxiphoid approach or a more extensive surgical exposure made to perform other corrective procedures. The distal end of the epicardial lead formed with one or two electrodes and an active fixation mechanism supported by an electrode head is affixed to the epicardium. Typically, the active fixation mechanism comprises the single electrode or one of the bipolar electrodes, but can be separate and electrically isolated from the electrodes.

Epicardial pacing and cardioversion/defibrillation leads were the first to be implanted widely, because endocardial leads lacked effective active or passive fixation mechanisms and relied upon relatively stiff lead bodies that cause perforations and dislodgement of the distal electrode(s). Initially, access to the epicardium was made by a thoracotomy or median sternotomy and excision through or removal of the pericardial sac. Typically, pace/sense electrodes penetrated the myocardium and were sutured against the epicardium to maintain fixation. The large patch electrodes of cardioversion/defibrillation electrodes were sutured to the epicardium.

Many improvements were made in epicardial pace/sense leads to minimize surgical trauma of accessing the epicardium and to avoid the need to suture the electrode to the epicardium. Thus, active fixation mechanisms of epicardial pacing leads typically comprise a tissue penetrating, self-affixing mechanism extending away from a support or base or plate of the electrode head. The fixation mechanism is forced into the myocardium typically employing an introduction tool engaging the electrode head until it is fully seated within the endocardium and the plate bears against the epicardium. The plate is typically formed with a tissue ingrowth encouraging fabric or lattice, whereby tissue ingrowth about the plate assists in chronic anchoring to the heart.

Such active fixation mechanisms include a rigid helix having a sharpened tip that is coupled with a lead conductor within the electrode head and extends at a right angle from the plate as typified by the MEDTRONIC® Model 6917 lead and the leads disclosed in commonly assigned U.S. Pat. Nos. 3,737,579 and 4,010,758. Other variations of such epicardial screw-in leads include multiple co-axial and intertwined helixes or a helix axially surrounding a pin extending coaxially with the helix axis from the electrode head. During implantation, the lead body and electrode head are mounted to an elongated tool, and the sharpened tip of the helix is advanced through the incision to perforate the epicardium. The tool and lead are rotated to screw the helix in until the plate abuts the epicardium, and the electrode head is detached from the tool.

A further epicardial screw-in lead is disclosed in commonly assigned U.S. Pat. No. 4,357,946 wherein the helix is mounted to a gear mechanism within the electrode head. The helix can itself be rotated to screw into the myocardium without rotating or moving the electrode head by a rotation of a removable stylet extending through the length of the lead body and engaging the gear mechanism. Both unipolar and bipolar embodiments are disclosed.

A further active fixation, unipolar, epicardial lead comprises the MEDTRONIC® Model 6951 lead disclosed in commonly assigned U.S. Pat. No. 4,313,448. The active fixation mechanism comprises forward facing barbed electrode having the tip at a predetermined angle with relation to the shank of the electrode and with respect to a flexible base pad or plate of the electrode head. The plate has a substantially centered hole and a plurality of outer holes for fibrous ingrowth, and the shank of the electrode extends out through the substantially centered hole. The barbed electrode is pushed into the myocardial tissue to the point where the base pad engages against the epicardium thereby indicating full implantation within the myocardium. During implantation, a stiffening stylet is employed to stiffen the lead body and a forceps is employed to grasp the electrode head to push the barb into the myocardium.

Over the years, endocardial pacing leads were improved by incorporation of effective active and passive fixation mechanisms, and development of simplified introduction procedures, stronger, more flexible, smaller diameter, and more reliable lead bodies enabling fixation of pace/sense electrodes in the right atrium, right ventricle and within the coronary sinus and great vein descending from the coronary sinus. Endocardial cardioversion/defibrillation leads were also developed incorporating these improved features of pacing leads and elongated cardioversion/defibrillation electrodes for implantation in the same locations. Thus, endocardial pacing and cardioversion/defibrillation leads have largely supplanted epicardial pacing and cardioversion/defibrillation leads in clinical practice. Epicardial pacing leads are still medically indicated for many patients, particularly children. Although the various indications for epicardial lead fixation in pediatric patients are numerous, some common factors include small stature, congenital heart defects with residual or potential right to left shunting or single ventricle hearts, or lack of venous access to the chamber requiring pacing.

Moreover, endocardial pacing and cardioversion/defibrillation leads cannot be implanted within the left heart chambers, due to risk of embolized thrombus. In particular, blood flows through the right heart chambers (atrium and ventricle), through the lungs, through the left heart chambers (atrium and ventricle) and then through the rest of the body, including the brain, before returning again to the right atrium. Implanted objects, however, often cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge, usually without serious risk. Consequently, endocardial leads are directed through the coronary sinus to locate pace/sense or cardioversion/defibrillation electrodes in the coronary sinus or great vein in order to pace and sense and/or cardiovert/defibrillate the left heart.

In spite of the difficulties, there remains a great need to be able to locate the electrode of a cardioversion/defibrillation lead at other left heart sites so that cardioversion/defibrillation shocks are delivered efficiently across the left ventricle.

Moreover, the left heart accounts for the majority of hemodynamic output. The left ventricle has a greater wall thickness (10-20 mm as compared to 1-5 mm) than the right ventricle because the left ventricle of the heart must pump oxygenated blood throughout the body while the right ventricle only pumps venous blood through the lungs to be oxygenated. Because the left heart is relatively more important for hemodynamic output, not surprisingly, various pathologies may be better treated through pacing of the left heart. For example, in patients with dilated cardiomyopathy and heart failure, electrical stimulation of both the right and left heart chambers has been shown to be of major importance to improve the patient's well being and manage heart failure. See, for example, Cazeau et al., "Four Chamber Pacing in Dilated Cardiomyopathy," *PACE*, November 1994, pgs. 1974-79. See also U.S. Pat. Nos. 5,716,392, 5,902,324 and 6,219,579 that provide right and left heart chamber pacing of heart failure patients.

As noted above, implantation of epicardial leads, is through general thoracic surgery; either via a median sternotomy; intercostal approach; or, in a more limited procedure, a sub-xiphoid approach. All of these procedures, however, involve major surgery, which may be painful and dangerous for the patient, as well as extremely costly. The sub-xiphoid approach, moreover, only permits limited access to the anterolateral surface of the left ventricle and does not provide any access at other locations of the left ventricle or the left atrium. A simpler, safer and more effective way of accessing the left side of the heart, including both the atrium and the ventricle with a medical electrical lead is needed.

The advent of thoracoscopy in cardiac surgery has shown promise as a technique to enable surgeons to implant epicardial leads without sternotomy or thoracotomy. Thoracoscopy normally involves penetration of the chest cavity with two or more tubular introducers that are passed through small incisions in the chest wall. Illumination devices, cutting instruments, sutures, etc. may be inserted into the chest cavity via the introducers. Approaches to accessing other sites of the left heart through the use of a thoracoscope and various tools are described in the above-referenced '392 patent and in U.S. Pat. Nos. 5,871,532 and 5,464,447, for example.

The above-described, conventional, active fixation, epicardial leads utilize a widened mesh pad that is normally disk-shaped and that provides a stop to prevent further insertion of a screw or hook fixation mechanism and a surface to encourage tissue ingrowth that enhances chronic fixation. These disk-like pads may present the surgeon with certain difficulties during insertion via a typical thoracoscopy introducer. There is the potential for the suture pad to resist movement through the introducer, and the lead may be damaged in the insertion. To avoid the potential for snagging the lead, surgeons may have to use a larger than necessary introducer or trocar, resulting in a larger incision, more scarring, and potentially more post-operative pain for the patient.

To avoid these problems, the above-referenced commonly assigned '392 patent discloses an epicardial lead having a "ski-shaped" needle, a strand of between 1-5 cm attached to the needle, an electrode attached to the strand, and an insulated lead body attached to the electrode. In addition, a test wire is also attached to the needle to permit the electrical characteristics of tissue to be ascertained before the lead is fully inserted. In an alternate embodiment the strand may feature a fixation helix. Due to the shape of the needle and the relatively short strand, the lead is particularly suitable for implantation to a heart using minimally invasive procedures, such as trocar and a thoracoscope. However, the suturing remains complicated and difficult to perform through the trocar.

In the '532 patent, an epicardial lead is disclosed having an active fixation mechanism for securing the electrode to the left heart that is introduced and deployed employing a thoracoscopy. A hook having a first longitudinally projecting piercing member is provided that has a first end that is pivotally coupled to a tubular housing that is coupled to the lead and has a lumen. A portion of the first end of the hook is disposed in the lumen, and the hook is pivotable between a first position wherein the first piercing member is disposed in spaced apart relation to the housing and a second position wherein the first piercing member is disposed proximate to the housing. A biasing member is coupled to the housing to bias the hook to the first position. The hook pivots to the second position in response to application of axial force to the portion of the first end to avoid piercing engagement with the heart, and pivots to the first position when force is removed so that the first piercing member of the hook may engage the heart.

The '447 patent discloses the use of a thoracoscope to introduce epicardial cardioversion/defibrillation electrodes into engagement against the left ventricular epicardium and to surgically staple it in place. Access to the pericardium and heart is through small multiple opening sites (under 12 mm diameter) made in the chest and xiphisternal area. In particular, a subxiphoid opening, such as an incision or puncture, is used for insertion of defibrillator electrodes, while an opening, such as an incision or puncture, between the 2nd rib and the 6th rib of a patient is used for observation via a thoracoscope. The exact location of the incision or opening is dependent upon a patient's particular anatomy. A trocar is inserted into the latter opening to facilitate the insertion and withdrawal of the thoracoscope and/or instrumentation. The defibrillator electrodes may also be manipulated through this latter opening. A third opening may be used for additional instrumentation and thoracoscopic observation as well as the later placement of a chest drainage tube. The defibrillator electrode is prepared for insertion by rolling it into a rolled shape with a pair of handles and then using the handles to insert the rolled defibrillator electrode through the latter opening or trocar. The defibrillator electrode includes a conductive wire mesh with a silicone backing, the silicone backing having a tail attached thereto. This allows the electrode to be pulled into place and then manipulated within the pericardium. The base of the tail can also be used as an attachment point for single point fixation. After proper placement of the electrode, permanent fixation with titanium staples is performed. In an alternative embodiment of a defibrillator electrode, a silicone insulator is positioned between a conductive wire mesh and a nonconductive mesh. A tail is attached to the nonconductive mesh.

Despite these improvements a need exists for a simple way to attach a pace/sense electrode of a pacing lead to the epicardium through a small diameter trocar or incision in a thoracoscopy where it is not necessary to manipulate the lead body or an active fixation mechanism.

Further epicardial pacing leads are disclosed in commonly assigned U.S. Pat. Nos. 4,282,886 and 4,768,523, wherein the fixation is effected by adhesives on the plate of the electrode head that polymerize upon exposure to body fluids and adhere with the epicardium. Cyanoacrylate surgical adhesive is employed in the '886 patent, and hydrogels are employed in the '523 patent. Hydrogels constitute a broad class of materials, which swell extensively in water but are not completely water-soluble. Partially dehydrated hydrogels, in which the hydrogel polymers contain controlled cross-linking, exhibit excellent adhesive properties, particularly in attaching to moist body tissue. The adhesive qualities of the hydrogels are affected by the degree of water content of the hydrogel. Aggressive adhesion develops during the initial phase of tissue contact when the hydrogel is hydrating or rehydrating.

Therefore, because these adhesives attach the plate to the epicardium upon contact, they prevent the testing of the optimal site of stimulation or sensing lead location. It is desirable to be able to press the pace/sense electrode against the epicardium and test the pacing and sensing thresholds before permanent fixation is effected, and that is not possible using such adhesives.

U.S. Pat. No. 6,121,341 discloses formation of a barrier over tissue or adhering tissues together or adhering implants to tissue in a process that involves applying or staining the tissue with a photoinitiator, then applying a polymer solution or gel (having added thereto a defined amount of the same or a different photoinitiator), and exposing the applied components to light to effect polymerization in situ. It is asserted that the delivered components polymerize at the tissue surface, adhere to the surface, and form a gel in the rest of the applied volume on exposure to light of a predetermined activation wavelength. Broad statements are made that electrodes and other implantable medical devices can be adhered to tissue in this way, but the only described examples relate to a polystyrene 12 plate or a Pellethane extruded polyurethane sheet. No other specific structures are disclosed.

This use of two-component adhesives delivered to the site requires a relatively complicated delivery system. Presumably, a useful delivery system would require delivery of precise amounts of each component in a fluid state that would have to mix together at the site. This would be difficult to accomplish without having direct visualization of the delivery, the mixing, and the light-activation.

Thus, there remains a need for a simple way of affixing an electrode to a surface of a body organ, e.g., the epicardium, in a secure and noninvasive manner.

SUMMARY OF THE INVENTION

Therefore, the present invention provides a novel lead having a noninvasive fixation mechanism and methods of and systems for attachment of an electrode of the lead to a surface of a body organ, e.g., the epicardium, in a noninvasive manner. The epicardial lead is preferably adapted to conduct electrical stimulation from an implantable or external electrical stimulator to a site of the epicardium and to conduct electrical signals of the heart from the site to the implantable or external electrical stimulator comprising an elongated lead body extending from a lead body proximal end to a lead body distal end, an electrode head formed at the lead body distal end having a plate adapted to bear against the epicardium, the electrode head supporting a first distal electrode, and a fixation mechanism comprising a light-activated adhesive disposed upon the plate that is sensitive to a predetermined bandwidth of light to adhere the plate to the epicardium while the plate is applied against the epicardium.

The lead is preferably implanted by performing a thoracoscopy of the thorax of the patient to visualize the site of the epicardium through a thoracoscope and to provide a pathway to the site of the epicardium. While viewing the site of the epicardium through the thoracoscope, the electrode head is inserted through the provided pathway to apply the plate against the site of the epicardium, and the light-activated adhesive is exposed to a predetermined bandwidth of light to adhere the plate to the epicardium.

The insertion is preferably conducted employing an elongated introduction tool having proximal and distal tool ends that is selectively operable to grasp and release the electrode head and to conduct light of the predetermined bandwidth to the electrode plate. The electrode head is grasped with the introduction tool at the introduction tool distal end and inserted through the second pathway to apply the plate against the site of the epicardium. The light of the predetermined wavelength or bandwidth is directed through the introduction tool to the electrode plate to activate the light-activated adhesive and adhere the electrode head to the epicardium. A release mechanism of the introduction tool is then manipulated to release the electrode head.

The introduction tool preferably has an opaque sidewall enclosing a plurality of optical fibers having optical fiber proximal and distal ends distributed around the circumference of and within the sidewall of the introduction tool to extend lengthwise to the introduction tool distal end, whereby the plurality of optical fiber distal ends are capable of emitting light of the predetermined frequency in a substantially cylindrical emission pattern from the introduction tool distal end.

The predetermined wavelength or bandwidth is preferably ultraviolet (UV) light. The light-activated adhesive is preferably coated upon the plate of the electrode head in a viscous or tacky form and enclosed within a light-tight package opaque to the predetermined wavelength or bandwidth in the final stage of manufacture to minimize exposure to any ambient UV light until the package is removed for use in the procedures of the present invention.

A second distal electrode can be formed on the electrode head or the lead body proximal to the electrode head.

The elongated lead body is preferably formed with a strain relief proximal to the electrode head for absorbing strain placed on the lead body at or adjacent to the lead body proximal end from being transmitted to the electrode head at the lead body distal end and absorbing the strain induced in the lead body by movement of the body organ, e.g., the contraction and expansion of the heart.

The strain relief preferably comprises one or more loop of the lead body formed in a common plane that is parallel with the plane of the mesh plate, so that the loops lie against the epicardium adjacent to and extending from the site of attachment of the electrode head to the epicardium.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 4 is an illustration of the assembly of an epicardial lead of the present invention with an introduction tool of the present invention wherein the electrode head is applied against the epicardium and UV light beams are emitted to activate the light-activated adhesive on the mesh plate of the electrode head;

FIG. 5 is an illustration of the assembly of FIG. 4 wherein a light-emitting sheath is withdrawn proximally and a rod is advanced distally to release the electrode head from an introducer handle;

DETAILED DESCRIPTION OF THE PREFERRED EMBODIMENTS

In the following detailed description, references are made to illustrative embodiments for carrying out the invention. It is understood that other embodiments may be utilized without departing from the scope of the invention.

Figure 1:
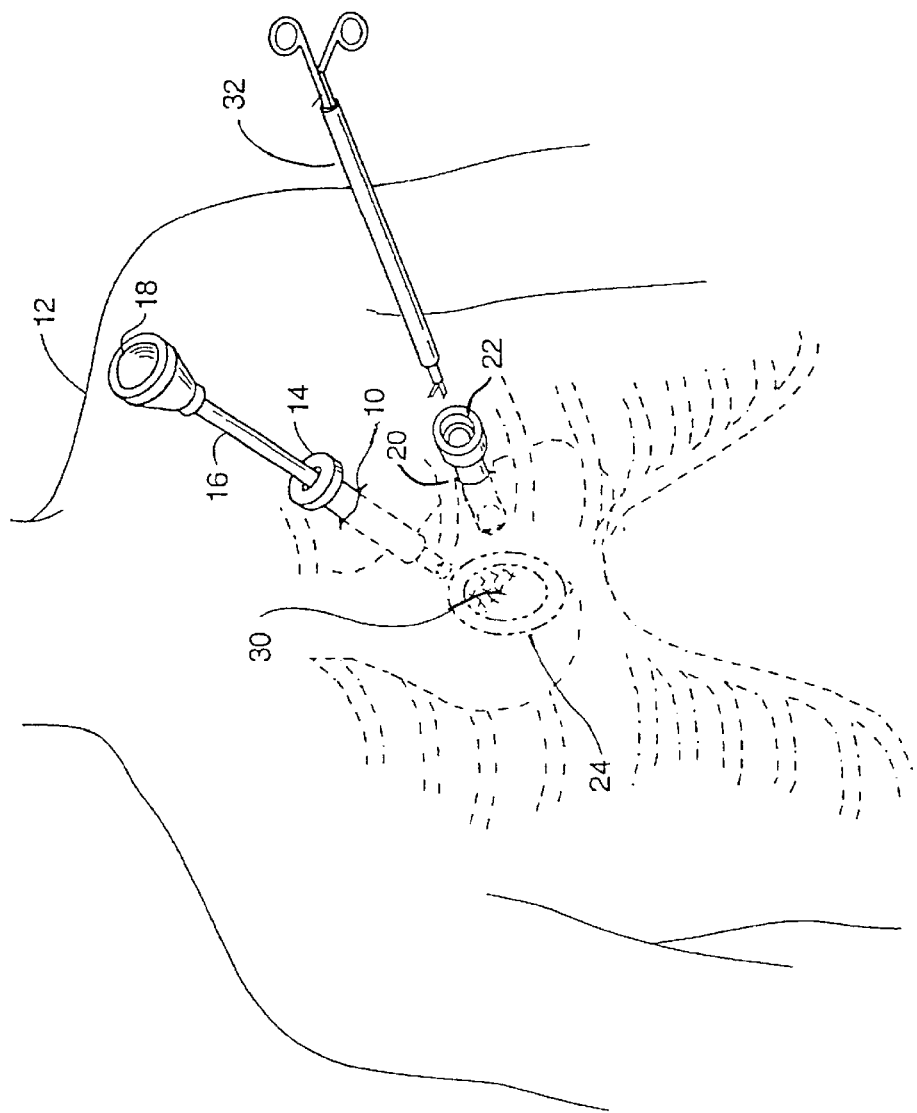
FIG. 1 is a schematic illustration of the tools employed in and the steps of a thoracoscopy to access a region of the left heart to enable implantation of epicardial leads in accordance with the present invention.

FIG. 1 illustrates the placement of trocars for both observation and insertion of pace/sense electrodes between the pericardium and selected sites of the left heart, particularly the left ventricle. A first opening 10, such as an incision or puncture, is made in a patient 12 between the patient's 2nd rib and 6th rib, for example. The exact location of the first opening 10 is dependent upon a patient's particular anatomy. The patient's left lung is deflated to allow unobstructed observation of the heart through the trocar 14. The deflation is accomplished by drawing a vacuum through a lung tube (not shown) that is inserted through the mouth or nose of the patient 12 into the left lung of the patient 12. After deflation, the peritoneal cavity is suffused with a gas, e.g., carbon monoxide, to pressurize the cavity to keep it open and sterile. The pressurized gas keeps the deflated lung away from the left heart so that the left heart can be viewed and accessed and provides a working space for the manipulation of the tools and epicardial leads of the present invention.

A thoracoscope 16 is then inserted into the trocar 14 to permit observation by a surgeon directly through an eyepiece 18 or indirectly through incorporation of a miniaturized video camera at the distal end of the thoracoscope 16 or optically coupled to the eyepiece 18 that is in turn coupled to an external video monitor (not shown). The thoracoscope also incorporates a light source for illuminating the cavity with visible light so that the epicardial surface can be seen directly or indirectly. Such a thoracoscope is described in the above-referenced '392, '447, and '532 patents.

A second opening 20 is then made, such as an incision or puncture, that is intercostal, i.e., between the ribs, in this illustration. A second trocar 22 is inserted through the second incision to point upward toward the pericardium 24 to enable the introduction of the epicardial lead of the present invention. The second opening 20 can be made in other locations in order to more readily access more cephalad and/or posterior sites of the left heart as shown in the above-referenced '392 and '532 patents and in a subxiphoid approach.

A third opening may be made and used to accommodate further trocar for additional instrumentation or thoracoscopic observation or infusion of sterilizing gas as well as later placement of a chest drainage tube.

The present invention can be practiced to adhere a pace/sense electrode to either the pericardium 24 or the epicardium 30 of the heart. For convenience the following description assumes that the electrode is to be adhered to the epicardium 30, but it will be understood that the electrode could be adhered to the pericardium.

Thus, the pericardial sac of the pericardium 24 surrounding the heart is perforated or excised through use of an endoscopic type cutting instrument 32 introduced through the second trocar 22 (or third trocar if present) as shown in FIG. 1 so that the epicardium 30 is exposed at the site where the pace/sense electrode of the pacing lead is to be affixed. If right and left heart pacing is to be provided for a patient suffering from congestive heart failure, then the pace/sense electrode of the epicardial lead would be attached to the epicardium near the AV junction of the left heart to provide global separation from a pace/sense electrode of an endocardial lead lodged within the right ventricle in order to restore synchronous contraction of the right and left ventricles.

Figure 2:
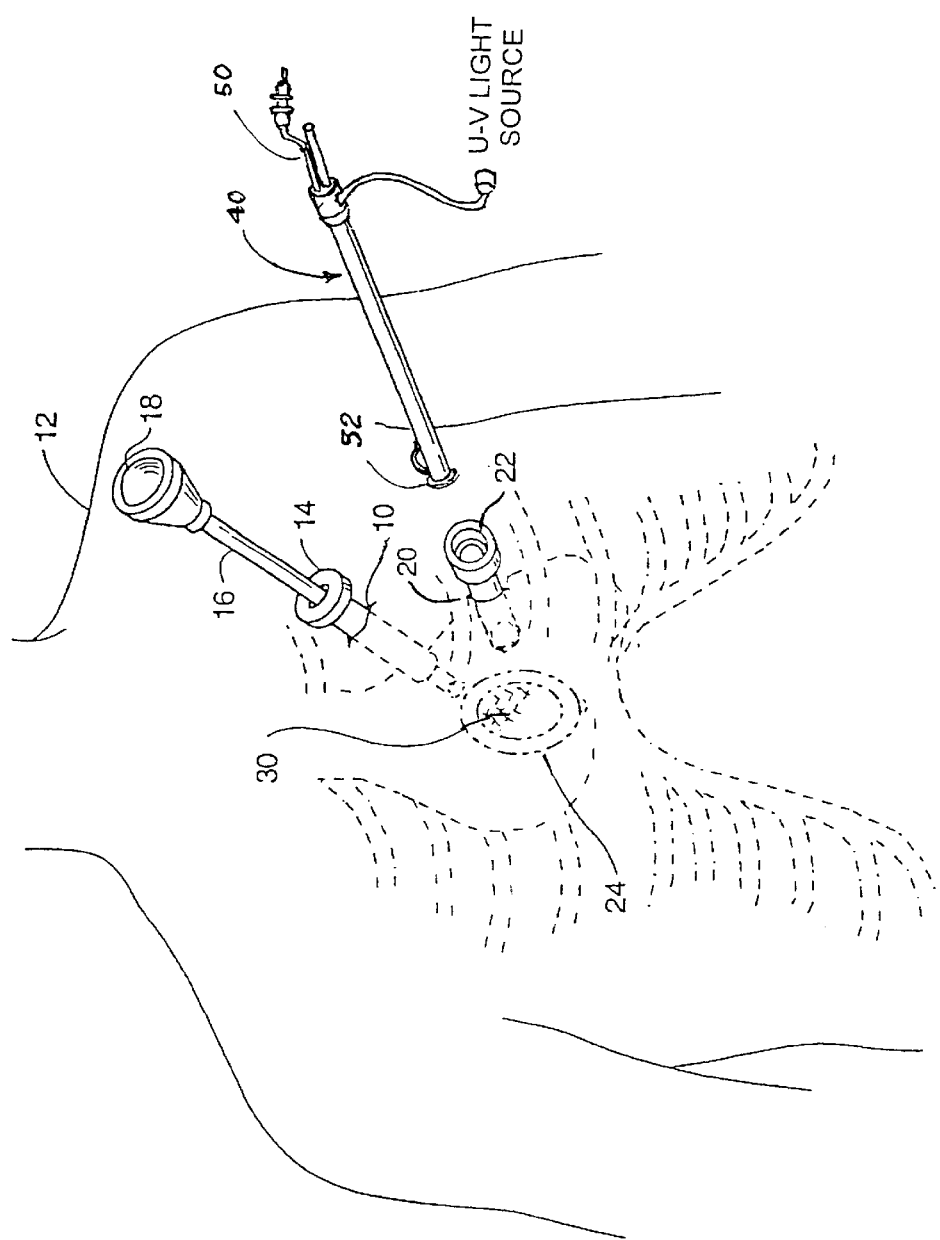
FIG. 2 is a schematic illustration of the assembly of an epicardial lead of the present invention with an introduction tool of the present invention positioned to commence implantation.

As explained further herein, an introduction tool 40 is utilized to insert the epicardial lead 50 through the second trocar 22 and orient the plate 52 of the electrode head 54 against exposed epicardium as shown in FIG. 2. Testing is then conducted to determine that the left ventricle is captured at an acceptable pacing pulse energy and that the cardiac signals traversing the left ventricle can be reliably detected. After an optimal site is determined, the electrode head is maintained against the epicardium at that site. The light-activated adhesive on the plate 52 of the electrode head 54 is illuminated with UV light causing the adhesive to polymerize and adhere the electrode head 54 to the epicardium. The introduction tool 40 is then manipulated to release the electrode head 54 and withdrawn from the second trocar 22. The lead body 56 is then routed subcutaneously to locate the lead body proximal end at the site of implantation of the pacing IPG to be attached with it in a manner well known in the art. The same procedure may be employed to implant a plurality of epicardial leads with epicardial pace/sense electrode(s) located at a plurality of sites of the epicardium 30 of the left and right heart accessed in the thoracoscopy.

Figure 3:
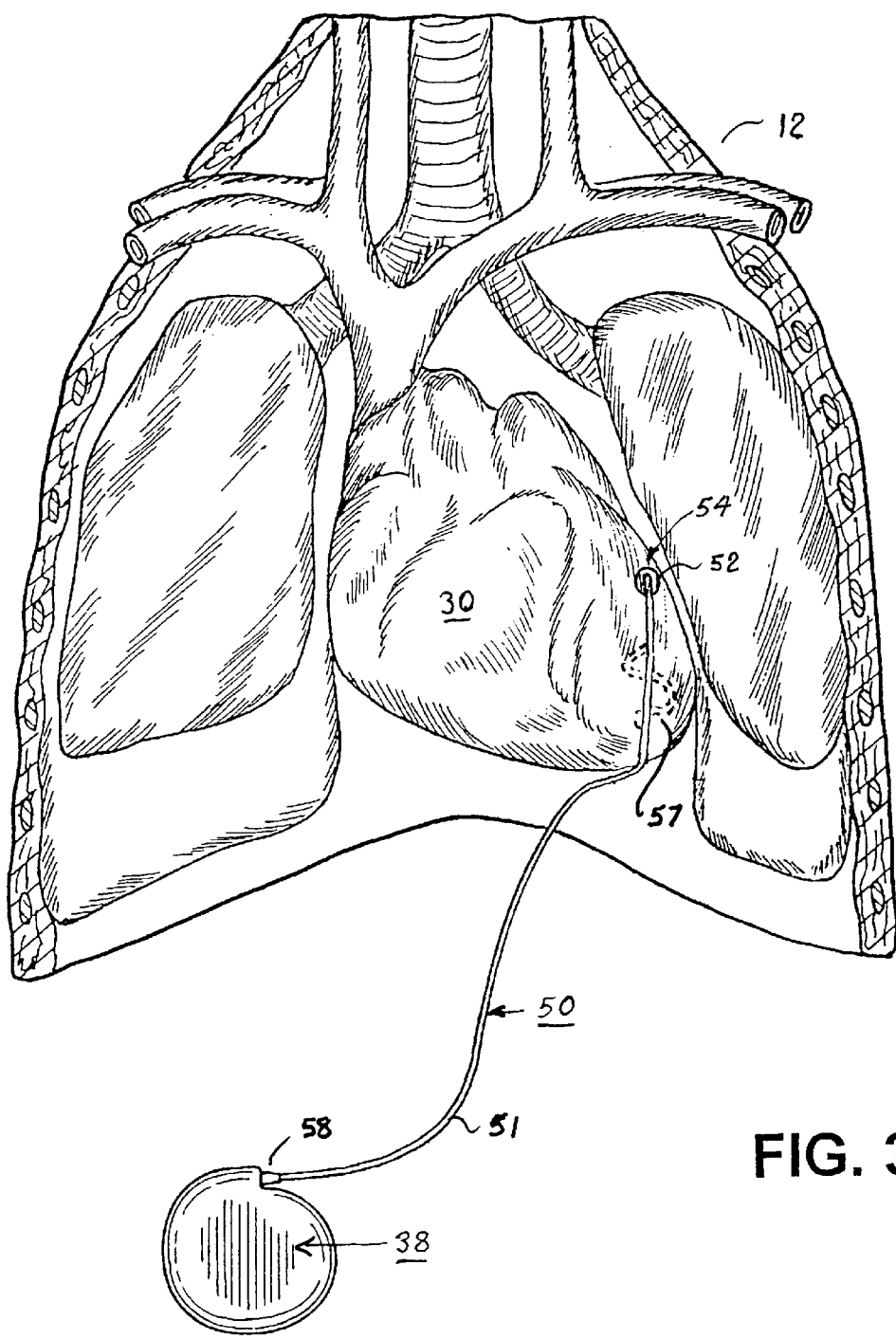
FIG. 3 is a schematic illustration of the distal electrode head of an epicardial lead of the present invention affixed to the epicardium of the left heart at a site close to the boundary of the left atrium with the left ventricle and the proximal lead connector coupled with an IMD IPG.
Figure 6:
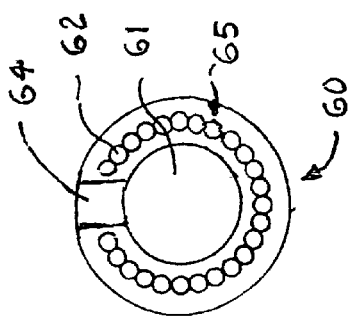
FIG. 6 is an end view of the light emitting sheath showing the distribution of light pipes to enable the emission of UV light beams as shown in FIG. 4.
Figure 7:
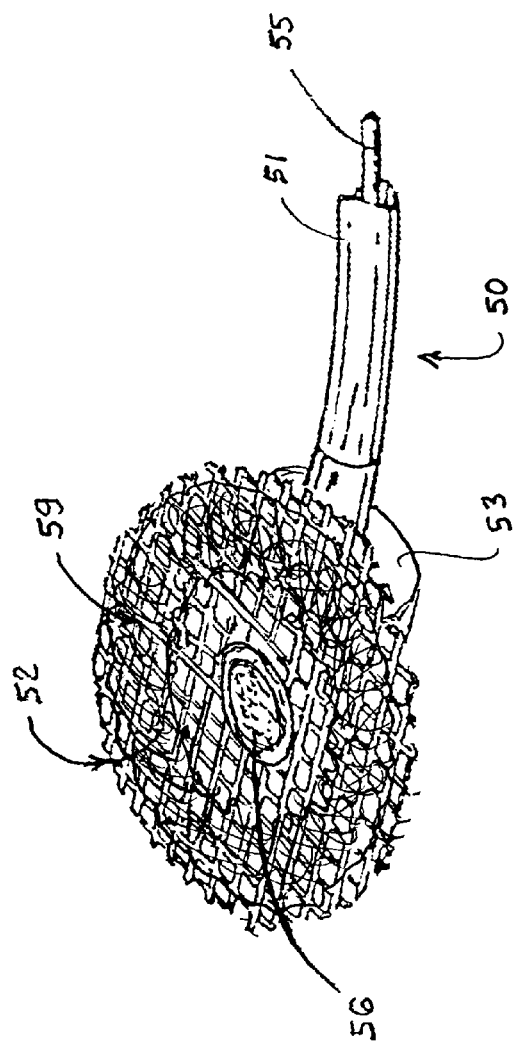
FIG. 7 is an expanded view of the electrode head of an epicardial lead of the present invention.

The thoracoscope 16, the first and second trocars 14 and 22, and any other instruments are withdrawn, the skin incisions are closed (although a drainage tool may be left in place through one of the skin incisions), the patient's lung is inflated, and the lung tube is withdrawn. The lead 50 extending between the attachment site of the epicardium 30 and the pacemaker IPG 38 is depicted in FIG. 3. It will be understood that the lead 50 can be a unipolar or bipolar epicardial lead, and that other epicardial and endocardial leads can extend from the IPG 38 to various locations on the epicardium 30 and within a heart chamber or coronary vessel. The lead 50 and other leads can be extended subcutaneously to the IPG that can be implanted abdominally or at other locations of the thorax.

The preferred embodiment of a unipolar epicardial lead 50 and the introduction tool 40 employed in the above-described procedure is depicted in FIGS. 4 through 7. The epicardial lead 50 comprises a lead body 51 enclosing at least one lead conductor 55 extending between the distal electrode head 54 and the connector element 58 at the lead body proximal end. The electrode head 54 comprises a boot 53 supporting the generally planar and circular mesh plate 52 and a centrally disposed pace/sense electrode 56 which may be flush with or project slightly from the plate 52. The boot 53 also encloses the electrical connection of the distal end of the lead conductor 55 with the pace/sense electrode 56. The electrode head 54 is preferably constructed so that it supports the mesh plate 52 parallel to the lead body axis and the electrode 56 at a 90° angle to the lead body axis to reduce the overall profile of the electrode head 54 and to reduce tension that would be applied to through the lead body to the mesh plate 52. However, the electrode head could be constructed so that the electrode 56 is axially aligned with the lead body and the plate 52 is at a 90° angle to the lead body axis, particularly if stress relief is incorporated into the lead body just proximal to where it joins the electrode head 54.

The mesh plate 52 comprises a Dacron mesh or the like that surrounds the electrode 56 and is impregnated or coated with a light-activated adhesive 59 over the entire surface of the mesh plate or in a band (FIG. 7) that is caused to polymerize when exposed to intense UV light and body fluids and adheres to body tissue, that is the pericardium 24 or epicardium 30, in this medical application.

More particularly, the light-activated adhesive preferably comprises one of a light-activated acrylic or cyanoacrylate adhesive, e.g., those offered by Loctite Corporation, Rocky Hill, Conn. Versions of such Loctite® acrylic adhesives and Loctite® FlashCure™ cyanoacrylate adhesives are available that cure upon exposure to low, medium, and high levels of UV light. The Loctite® FlashCure™ cyanoacrylate adhesives are cured under conditions where the adhesive is both moistened and exposed to the requisite level of UV light, which can be provided in the practice of the present invention. The light-activated adhesive layer 59 can be applied to the mesh of plate 52 in a viscous state and in metered amount by a dispenser available from Loctite Corp. Then, the electrode head 54 can be enclosed within an opaque and moisture sealed package that is removed just prior to implantation in accordance with the present invention.

Alternatively, the method of the present invention contemplates that the light-activated adhesive could be supplied in a container with the lead so that the physician can dispense it in a viscous state in a layer on the mesh plate 52.

The introduction tool 40 comprises a mechanism for grasping the electrode head 54 to aim and guide the pace/sense electrode 56 and mesh plate 52 toward the epicardial implantation site, to apply UV light and pressure to the mesh plate 52 to effect adhesion of the mesh plate 52 to the epicardium 30, and to release the lead body and electrode head 54 when adhesion is effected. To accomplish these functions, the introduction tool 40 preferably takes the form of those employed to affix epicardial screw-in electrodes but modified to transmit UV light to the light-activated adhesive on the mesh plate 52. For example, the introduction tool 40 may take the form of the instruments disclosed in commonly assigned U.S. Pat. No. 4,280,510 but modified in accordance with the invention to transmit UV light or to the light-activated adhesive on the mesh plate 52 around the electrode 56.

In particular, and in reference to FIGS. 4-7, the introduction tool 40 comprises an elongated tubular handle 46 having a notched distal end 47 that is shaped to frictionally grip the sides of the boot 53 of the electrode head 54 and a slot 48 that loosely receives the lead body 51. The handle 46 also includes a handle lumen 49 extending from the notched distal end 47 to a lumen opening at the handle proximal end 44.

An ejection rod 70 is fitted into the handle lumen 49 so that its distal end can be advanced against the boot 53 by applying pressure to its proximal end to release the boot 53 from the notched distal end 47 when adhesion is accomplished.

An outer tubular sheath 60 is formed with a sheath lumen 61 through which the lead body 51, the tubular handle 46, and the rod 70 are inserted as shown in FIG. 4. The lead body 51 is maintained within the slot 48 by the sheath wall 65 of sheath 60 except for a distal portion that passes out through the slot 64 in the distal portion of the sheath wall 65. In this way, the assembly of the lead 50 and the introduction tool 40 can be inserted through the trocar 22 to press the pace/sense electrode 56 and the mesh plate 52 against the epicardium 30 as shown schematically in FIG. 4.

The outer sheath wall 65 is opaque and encloses a plurality of optical fibers or light pipes 62 extending lengthwise from a proximal sheath hub 66 to the sheath distal end 69. The proximal ends of the light pipes 62 are gathered together within hub 66 and coupled with a flexible light pipe extension cable 68 that is adapted to be coupled with a source of UV light.

The UV light beams 80 are emitted from the exposed distal ends of the light pipes 62 which are situated just proximal to the mesh plate 52 when the mesh plate 52 and pace/sense electrode 56 are pressed against the epicardium 30 as shown in FIG. 4. The light beams 80 impinge on the light-activated adhesive disposed on the mesh plate 52 and cause it to adhere to the epicardium in the manner described above. The adhesion is effected in a matter of seconds, and then the UV light is extinguished. The sheath 60 is withdrawn as shown in FIG. 5 while the rod 70 and handle 46 are held stationary. The handle 46 is then held stationary as the rod 70 is advanced slightly distally 49 to release the boot 53 from the notched distal end 47 of the handle. The handle 46 and the rod 70 are then withdrawn from the trocar 22, and the lead body 51 and lead connector 58 are tunneled to the site of the IPG 38. The lead body may extend through the incision or opening 20 and tunneled subcutaneously from there to an IPG 38 implanted subcutaneously at an upper thoracic site. Or the lead body 51 and lead connector 58 may be routed through an more sub-xiphoid route obtained by use of a third, sub-xiphoid incision and trocar and then subcutaneously to an abdominal site of implantation of the IPG 38 as shown schematically in FIG. 3.

The lead body 51 can also be pre-formed with a series of loops 57 shown in broken lines in FIG. 5 to provide strain relief of strain imposed longitudinally along the length of the lead body 51 that could dislodge the electrode head 56, particularly in the acute post-operative period before tissue encapsulation of the electrode head 54 occurs to more firmly hold it in place. The loops 57 absorb strain placed on the lead body 51 at or adjacent to the lead body proximal end from being transmitted to the electrode head 54 and absorbing the strain induced in the lead body 51 by the contraction and expansion of the heart.

The loops 57 would be formed in a common plane that is parallel with the plane of the mesh plate 52, so that the loops 57 would lie against the epicardium 30 adjacent to the site of attachment of the electrode head 56 as shown in broken lines in FIG. 3. The loops 57 would straighten out when the lead body 51 is confined within the handle slot 48.

It will also be understood that the lead 50 could be formed as a bipolar epicardial lead having a further electrode located upon the mesh plate 52 or upon the boot 53 or disposed along the length of the lead body 51. The second electrode could comprise a conductive ring or coil along the lead body at the loops 57.

The pace/sense electrode 56 is generally disc or ring shaped and can be formed of any of the known electrode materials, e.g., a Pt-Ir alloy, activated carbon, titanium nitride, or a porous platinized steroid eluting electrode exhibiting an effective surface area in the range of 0.1 to 4.0 mm$^2$, and preferably between 0.6 to 3.0 mm$^2$.

Conclusion

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of epicardial leads that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A medical electrical lead adapted to conduct electrical stimulation from an implantable or external electrical stimulator to a site of the epicardium and to conduct electrical signals of the heart from the site to the implantable or external electrical stimulator comprising:

an elongated lead body extending from a lead body proximal end to a lead body distal end;

an electrode head formed at the lead body distal end having a plate adapted to bear against the epicardium, the electrode head supporting a first distal electrode; and a fixation mechanism comprising a light-activated adhesive disposed upon the plate that is sensitive to a predetermined bandwidth of light to adhere the plate to the epicardium while the plate is applied against the epicardium.

2. The medical electrical lead of claim 1, wherein the light-activated adhesive comprises one of a light-activated acrylic or cyanoacrylate adhesive that is activated by ultraviolet light.

3. The medical electrical lead of claim 2, wherein the plate of the electrode head is formed of a light transmissive fabric mesh upon which the light activated adhesive is disposed, whereby the ultraviolet light is transmitted through the light transmissive fabric mesh.

4. The medical electrical lead of claim 3, wherein the light activated adhesive is disposed in a band substantially surrounding said first distal electrode.

5. The medical electrical lead of claim 1, wherein the plate of the electrode head is formed of a light transmissive fabric mesh upon which the light activated adhesive is disposed, whereby light of the predetermined bandwidth is transmitted through the light transmissive fabric mesh.

6. The medical electrical lead of claim 5, wherein the light activated adhesive is disposed in a band substantially surrounding said first distal electrode.

7. The medical electrical lead of claim 1, wherein the light activated adhesive is disposed in a band substantially surrounding said first distal electrode.

8. The medical electrical lead of claim 1, wherein the elongated lead body is formed with a strain relief proximal to the electrode head for absorbing strain placed on the lead body at or adjacent to the lead body proximal end from being transmitted to the electrode head at the lead body distal end and absorbing the strain induced in the lead body by the contraction and expansion of the heart.

9. The medical electrical lead of claim 8, wherein strain relief comprises one or more loop of the lead body formed in a common plane that is parallel with the plane of the mesh plate, so that the loops lie against the epicardium adjacent to and extending from the site of attachment of the electrode head to the epicardium.

10. A method of implanting a medical electrical lead to conduct electrical stimulation from an implantable or external electrical stimulator to a site of the epicardium and to conduct electrical signals of the heart from the site to the implantable or external electrical stimulator comprising:

providing a medical electrical lead having:

an elongated lead body extending from a lead body proximal end to a lead body distal end;

an electrode head formed at the lead body distal end having a plate adapted to bear against the epicardium, the electrode head supporting a first distal electrode; and a fixation mechanism comprising a light-activated adhesive disposed upon the plate;

forming a incision through the thorax of the patient to access the site of the epicardium;

inserting the electrode head through the incision to apply the plate against the site of the epicardium; and exposing the light-activated adhesive to a predetermined bandwidth of light transmitted through the incision to adhere the plate to the epicardium.

11. The method of claim 10, wherein:

the inserting step further comprises:

providing an elongated introduction tool having proximal and distal tool ends that is selectively operable to grasp and release the electrode head and conducts light of the predetermined bandwidth to the electrode plate;

grasping the electrode head with the introduction tool at the introduction tool distal end; and manipulating the introduction tool at or adjacent the introduction tool proximal end to inserting the introduction tool and electrode head through the incision and apply the plate against the site of the epicardium; and the exposing step comprises conducting light of the predetermined bandwidth through the introduction tool to the electrode plate.

12. The method of claim 11, wherein the plate of the electrode head is formed of a light transmissive fabric mesh upon which the light activated adhesive is disposed, whereby light of the predetermined bandwidth is transmitted through the light transmissive fabric mesh.

13. The method of claim 12, wherein the light activated adhesive is disposed in a band substantially surrounding said first distal electrode.

14. The method of claim 11, wherein the light activated adhesive is disposed in a band substantially surrounding said first distal electrode.

15. The method of claim 11, wherein the elongated lead body is formed with a strain relief proximal to the electrode head for absorbing strain placed on the lead body at or adjacent to the lead body proximal end from being transmitted to the electrode head at the lead body distal end and absorbing the strain induced in the lead body by the contraction and expansion of the heart.

16. The method of claim 15, wherein strain relief comprises one or more loop of the lead body formed in a common plane that is parallel with the plane of the mesh plate, so that the loops lie against the epicardium adjacent to and extending from the site of attachment of the electrode head to the epicardium.

17. The method of claim 10, wherein the light-activated adhesive comprises one of a light-activated acrylic or cyanoacrylate adhesive that is activated by ultraviolet light.

18. The method of claim 17, wherein the plate of the electrode head is formed of a light transmissive fabric mesh upon which the light activated adhesive is disposed, whereby the ultraviolet light is transmitted through the light transmissive fabric mesh.

19. The method of claim 18, wherein the light activated adhesive is disposed in a band substantially surrounding said first distal electrode.

20. A method of implanting a medical electrical lead to conduct electrical stimulation from an implantable or external electrical stimulator to a site of the epicardium and to conduct electrical signals of the heart from the site to the implantable or external electrical stimulator comprising:

providing a medical electrical lead having:

an elongated lead body extending from a lead body proximal end to a lead body distal end;

an electrode head formed at the lead body distal end having a plate adapted to bear against the epicardium, the electrode head supporting a first distal electrode; and a fixation mechanism comprising a light-activated adhesive disposed upon the plate;

performing a thoracoscopy of the thorax of the patient to visualize the site of the epicardium through a thoracoscope and to provide a pathway to the site of the epicardium; and while viewing the site of the epicardium through the thoracoscope, inserting the electrode head through the provided pathway to apply the plate against the site of the epicardium; and exposing the light-activated adhesive to a predetermined bandwidth of light to adhere the plate to the epicardium.

21. The method of claim 20, wherein:

the inserting step further comprises:

providing an elongated introduction tool having proximal and distal tool ends that is selectively operable to grasp and release the electrode head and conducts light of the predetermined bandwidth to the electrode plate;

grasping the electrode head with the introduction tool at the introduction tool distal end; and manipulating the introduction tool at or adjacent the introduction tool proximal end to inserting the introduction tool and electrode head through the pathway and apply the plate against the site of the epicardium; and the exposing step comprises conducting light of the predetermined bandwidth through the introduction tool to the electrode plate.

22. The method of claim 21, wherein the plate of the electrode head is formed of a light transmissive fabric mesh upon which the light activated adhesive is disposed, whereby light of the predetermined bandwidth is transmitted through the light transmissive fabric mesh.

23. The method of claim 22, wherein the light activated adhesive is disposed in a band substantially surrounding said first distal electrode.

24. The method of claim 21, wherein the light activated adhesive is disposed in a band substantially surrounding said first distal electrode.

25. The method of claim 21, wherein the elongated lead body is formed with a strain relief proximal to the electrode head for absorbing strain placed on the lead body at or adjacent to the lead body proximal end from being transmitted to the electrode head at the lead body distal end and absorbing the strain induced in the lead body by the contraction and expansion of the heart.

26. The method of claim 25, wherein strain relief comprises one or more loop of the lead body formed in a common plane that is parallel with the plane of the mesh plate, so that the loops lie against the epicardium adjacent to and extending from the site of attachment of the electrode head to the epicardium.

27. The method of claim 20, wherein the light-activated adhesive comprises one of a light-activated acrylic or cyanoacrylate adhesive that is activated by ultraviolet light.

28. The method of claim 27, wherein the plate of the electrode head is formed of a light transmissive fabric mesh upon which the light activated adhesive is disposed, whereby the ultraviolet light is transmitted through the light transmissive fabric mesh.

29. The method of claim 28, wherein the light activated adhesive is disposed in a band substantially surrounding said first distal electrode.

30. The method of claim 20, wherein:
the step of performing a thoracoscopy further comprises:
forming first and second pathways through a patient's thoracic wall to access the site of the epicardium; and
inserting a thoracoscope through the first pathway surgically made through the patient's thoracic wall to visualize the site of the epicardium; and
the inserting step comprises inserting the electrode head through the second pathway to apply the plate against the site of the epicardium.

31. A system for implanting a medical electrical lead to conduct electrical stimulation from an implantable or external electrical stimulator to a site of the epicardium and to conduct electrical signals of the heart from the site to the implantable or external electrical stimulator comprising:
A medical electrical lead having:
an elongated lead body extending from a lead body proximal end to a lead body distal end;
an electrode head formed at the lead body distal end having a plate adapted to bear against the epicardium, the electrode head supporting a first distal electrode; and
a fixation mechanism comprising a light-activated adhesive disposed upon the plate;
means for forming first and second pathways through a patient's thoracic wall to access the site of the epicardium;
a thoracoscope adapted to be inserted through the first pathway surgically made through the patient's thoracic wall to visualize the site of the epicardium; and
means for inserting the electrode head through the second pathway to apply the plate against the site of the epicardium and to expose the light-activated adhesive to a predetermined bandwidth of light to adhere the plate to the epicardium.

32. The method of claim 31, wherein the inserting means further comprises an elongated introduction tool having proximal and distal tool ends that is selectively operable to grasp and release the electrode head and to conduct light of the predetermined bandwidth to the electrode plate and further comprising:
means for grasping the electrode head with the introduction tool at the introduction tool distal end to enable manipulation of the introduction tool at or adjacent the introduction tool proximal end to insert the introduction tool and electrode head through the second pathway and apply the plate against the site of the epicardium;
light conducting means for conducting light of the predetermined bandwidth through the introduction tool to the electrode plate; and
means for releasing the electrode head from the grasping means.

33. The system of claim 32, wherein the introduction tool has an opaque sidewall, and the light conducting means comprises a plurality of optical fibers having optical fiber proximal and distal ends distributed around the circumference of and within the sidewall of the introduction tool to extend lengthwise to the introduction tool distal end, whereby the plurality of optical fiber distal ends are capable of emitting light of the predetermined frequency in a substantially cylindrical emission pattern from the introduction tool distal end.

34. The system of claim 31, wherein the inserting means further comprises an elongated introduction tool that is selectively operable to grasp and release the electrode head and to conduct light of the predetermined bandwidth to the electrode plate and further comprising:
an elongated tubular handle extending from handle proximal and distal ends and having a handle lumen extending from the handle proximal end to the handle distal end, a notched distal end that is shaped to frictionally grip the electrode head, and an elongated slot extending to the handle proximal end that loosely receives the lead body;
an elongated ejection rod extending between an ejection rod proximal end to an ejection rod distal end fitted into the handle lumen so that the ejection rod distal end can be advanced through the handle lumen against the electrode head to release the electrode head from the notched distal end when adhesion is accomplished; and
an outer tubular sheath extending from a sheath proximal end to a sheath distal end and formed with a sheath lumen through which the tubular handle and the rod within the handle lumen are inserted to retain the lead body within the elongated slot, the outer tubular sheath further enclosing a light conductor having a light conductor proximal end and a light conductor distal end that conducts light of the predetermined bandwidth through the outer tubular sheath to the sheath distal end, whereby the light is emitted in a light beam from the light conductor distal end upon the light-activated adhesive.

35. The system of claim 34, wherein the tubular sheath has an opaque cylindrical sidewall, and the light conductor comprises a plurality of optical fibers having optical fiber proximal and distal ends distributed around the circumference of and within the sidewall to extend lengthwise to the sheath distal end, whereby the light conductor distal end comprises a like plurality of optical fiber distal ends capable of emitting light of the predetermined frequency in a substantially cylindrical emission pattern from the tubular sheath distal end.

36. The system of claim 31, wherein the light-activated adhesive comprises one of a light-activated acrylic or cyanoacrylate adhesive that is activated by ultraviolet light.

37. The system of claim 36, wherein the plate of the electrode head is formed of a light transmissive fabric mesh upon which the light activated adhesive is disposed, whereby the ultraviolet light is transmitted through the light transmissive fabric mesh.

38. The system of claim 37, wherein the light activated adhesive is disposed in a band substantially surrounding said first distal electrode.

39. The system of claim 31, wherein the plate of the electrode head is formed of a light transmissive fabric mesh upon which the light activated adhesive is disposed, whereby light of the predetermined bandwidth is transmitted through the light transmissive fabric mesh.

40. The system of claim 39, wherein the light activated adhesive is disposed in a band substantially surrounding said first distal electrode.

41. The system of claim 31, wherein the light activated adhesive is disposed in a band substantially surrounding said first distal electrode.

42. The system of claim 31, wherein the elongated lead body is formed with a strain relief proximal to the electrode head for absorbing strain placed on the lead body at or adjacent to the lead body proximal end from being transmitted to the electrode head at the lead body distal end and absorbing the strain induced in the lead body by the contraction and expansion of the heart.

43. The system of claim 42, wherein strain relief comprises one or more loop of the lead body formed in a common plane that is parallel with the plane of the mesh plate, so that the loops lie against the epicardium adjacent to and extending from the site of attachment of the electrode head to the epicardium.

* * * * *